United States Patent [19]

Aagardl Roger L. et al.

[11] Patent Number: 4,944,035
[45] Date of Patent: Jul. 24, 1990

[54] MEASUREMENT OF THERMAL CONDUCTIVITY AND SPECIFIC HEAT

[75] Inventors: Aagardl Roger L., Prior Lake; Ulrich Bonne, Hopkins; Robert J. Matthys, Minneapolis, all of Minn.

[73] Assignee: Honeywell Inc., Minneapolis, Minn.

[21] Appl. No.: 210,892

[22] Filed: Jun. 24, 1988

[51] Int. Cl.$^5$ ............... G06F 15/20; G01K 17/08
[52] U.S. Cl. ................... 364/556; 73/204.16; 73/204.17; 73/25.03; 364/557; 374/30; 374/44
[58] Field of Search .............. 364/556, 557, 558; 73/27 R, 204.14, 204.15, 204.16, 204.17, 204.33, 204.24, 204.25, 204.26; 374/43, 44, 1, 29, 144, 113, 166

[56] References Cited

U.S. PATENT DOCUMENTS

| | | | |
|---|---|---|---|
| 3,672,205 | 6/1972 | Leidenfrost | 374/44 |
| 3,821,895 | 7/1974 | Sunikawa et al. | 374/30 |
| 3,913,379 | 10/1975 | Ruez et al. | 73/27 R |
| 4,036,051 | 7/1977 | Feu et al. | 374/39 |
| 4,063,447 | 12/1977 | Mathison | 73/27 R |
| 4,123,934 | 11/1978 | Hoht | 73/27 R |
| 4,164,862 | 8/1979 | Jackson | 73/27 R |
| 4,254,654 | 3/1981 | Clouser et al. | 73/27 R |
| 4,381,154 | 4/1983 | Hammond, III | 374/43 |
| 4,461,166 | 7/1984 | Gatten et al. | 73/27 R |
| 4,478,076 | 10/1984 | Bohrer | 73/204.16 |
| 4,478,077 | 10/1984 | Bohrer et al. | 73/204.26 |
| 4,501,144 | 2/1985 | Higashi et al. | 73/204.26 |
| 4,594,879 | 6/1986 | Maeda et al. | 73/27 R |
| 4,630,938 | 12/1986 | Piorkowska-Palczewska et al. | 374/44 |
| 4,651,564 | 3/1987 | Johnson et al. | 73/204.26 |
| 4,683,159 | 7/1987 | Bohrer et al. | 428/138 |
| 4,697,165 | 9/1987 | Ishigurd et al. | 73/27 R |
| 4,734,641 | 3/1988 | Byrd, Jr. et al. | 374/44 |
| 4,735,082 | 4/1988 | Kolloff | 73/27 R |
| 4,739,657 | 4/1988 | Higashi et al. | 73/204.16 |
| 4,741,198 | 5/1988 | Farren et al. | 73/27 R |
| 4,783,996 | 11/1988 | Ohta et al. | 73/204.17 |
| 4,825,693 | 5/1989 | Bohrer et al. | 73/204.25 |

Primary Examiner—Kevin J. Teska
Attorney, Agent, or Firm—Gregory A. Bruns

[57] ABSTRACT

A method and apparatus for determining both the thermal conductivity, k, and specific heat, $c_p$, of a fluid of interest are disclosed. An embodiment uses proximately positioned resistive heater and thermal sensor coupled by the fluid of interest. A pulse of electrical energy is applied to the heater of a level and duration such that both a transient change and a substantially steady-state temperature occur in the sensor. The k of the fluid of interest is determined based upon a known relation between the sensor output and k at steady-state sensor temperature; and $c_p$ of the fluid of interest is determined based on a known relation among k, the rate of change of the sensor output during a transient temperature change in the sensor and $c_p$.

28 Claims, 10 Drawing Sheets

THERMAL DIFFUSIVITY SENSOR OR
SPECIFIC HEAT SENSOR

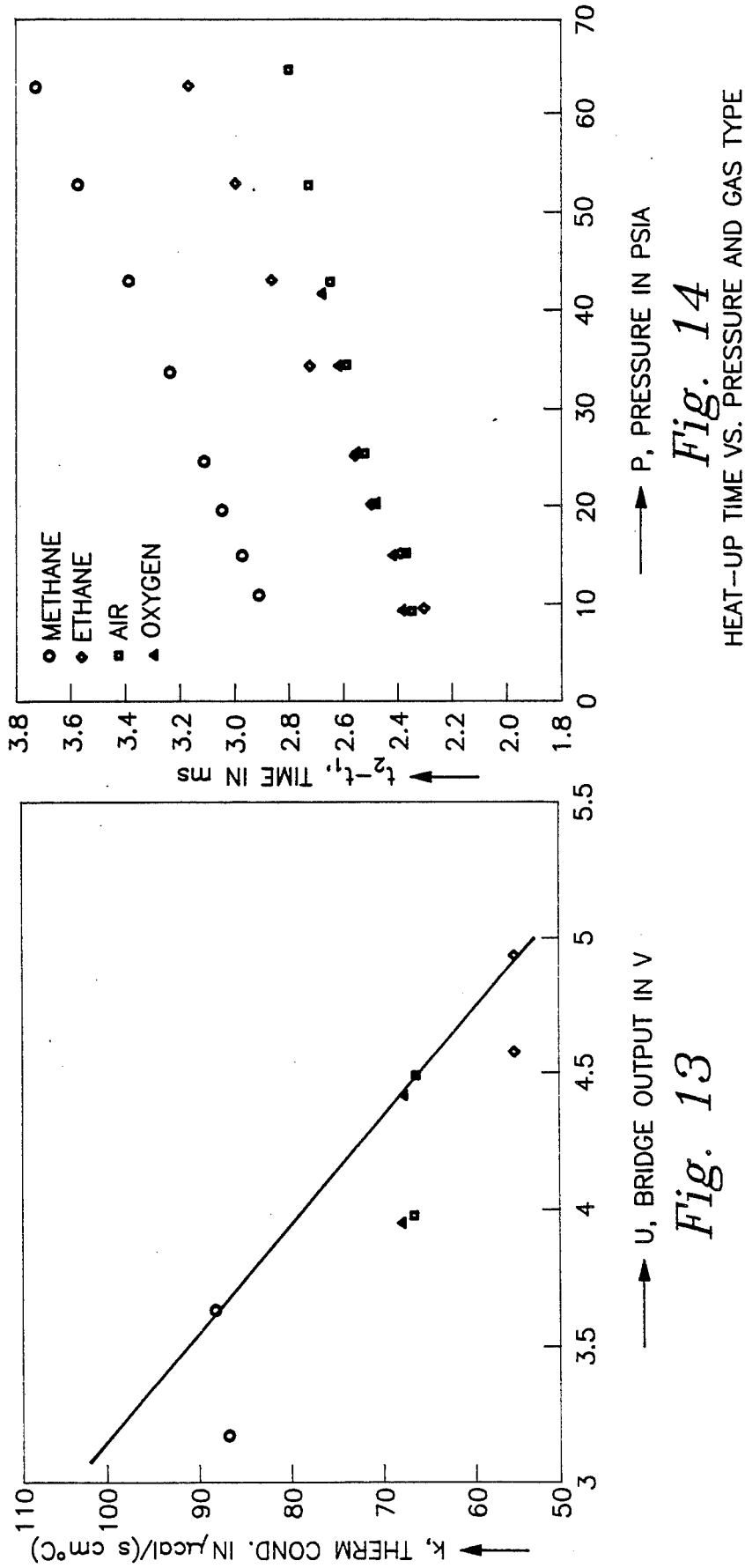

HEAT-UP TIME VS. PRESSURE AND GAS TYPE

HEAT-UP TIME VS. PRESSURE AND GAS TYPE

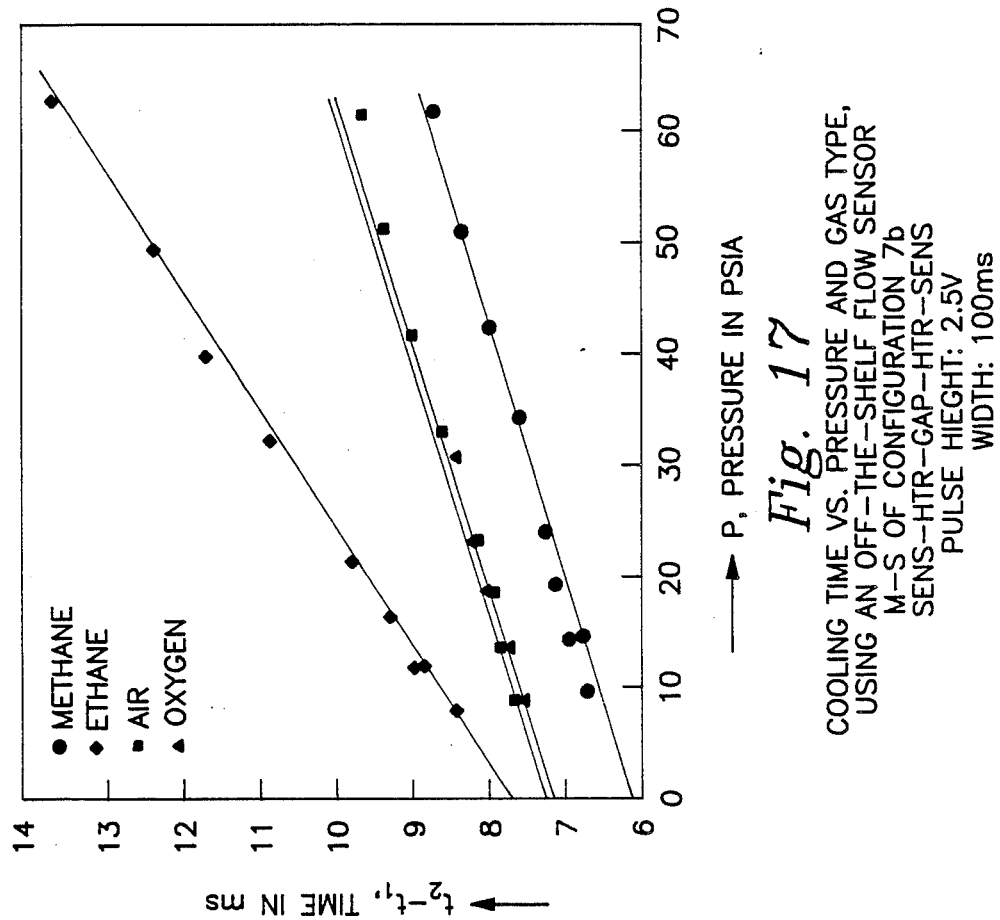
Fig. 17 COOLING TIME VS. PRESSURE AND GAS TYPE, USING AN OFF-THE-SHELF FLOW SENSOR M-S OF CONFIGURATION 7b SENS-HTR-GAP-HTR-SENS PULSE HEIGHT: 2.5V WIDTH: 100ms

MEASUREMENT OF THERMAL CONDUCTIVITY AND SPECIFIC HEAT

CROSS REFERENCE TO RELATED APPLICATIONS

Reference is made to two related applications Ser. No. 221,200 and 211,014 filed of even date and assigned to the common assigned of the present application.

BACKGROUND OF THE INVENTION

1. Field of the Invention

The present invention relates to the measurement of certain physical properties of fluids and, more particularly, to the determination of both the specific heat and thermal conductivity of gases. In a preferred embodiment a trapped gas sample transmits steady state and transient responses to input energy of limited duration which can be measured electrically as be extracting the influence of the input energy in the form of measureable change in temperature of an appropriate sensor in contact with the gas of interest.

2. Prior Art

In the prior art the traditional approach to determining specific heat, $c_p$, has been via calorimetry using reversible step increases of energy fed to a thermally isolated or adiabatic system. Such devices are bulky, slow and cumbersome. Little progress has been made towards the automation of a rapid method to make this determination.

With respect to measuring thermal conductivity in fluids various types of detectors have been used. This includes resistance bridge type sensors. One such device is described in U.S. Pat. No. 4,735,082 in which thermal conductivity is detected using a Wheatstone bridge technique in which a filment in one diagonal of the bridge is placed or positioned in a cavity through which the sample gas of interest is passed. The filament is used to introduce a series of amounts of thermal energy into the fluid of interest at alternating levels by varying the input voltage which, are, in turn, detected at the other diagonal as voltage difference signals. Integration of the changes of the value of the successive stream of signals yields a signal indicative of the heat dissipation through the fluid, and thus, the thermal conductivity of the fluid.

Further to the measurement of thermally induced changes in electrical resistance, as will be discussed in greater detail below, especially with reference to prior art FIGS. 1-5, recently very small and very accurate "microbridge" semiconductor chip sensors have been described in which etched semiconductor "microbridges" are used as condition or flow sensors. Such sensors might include, for example, a pair of thin film sensors around a thin film heater. Semiconductor chip sensors of the class described are treated in a more detailed manner in one or more of patents such as 4,478,076, 4,478,077, 4,501,144, 4,651,564 and 4,683,159, all of common assignee with the present invention.

It is apparent, however, that it has been necessary to address the measurement of specific heat $c_p$, and thermal condutance, k of a fluid of interest with separate and distinct devices. Not only is this quite expensive, it also has other drawbacks. For example, the necessity of separate instruments to determine specific heat and thermal conductivity may not allow the data consistency and accuracy needed for useful fluid process stream (gas or liquid) characterization because the required degree of correlation may not be present.

SUMMARY OF THE INVENTION

The present invention overcomes many disadvantages associated with the determination of both specific heat, $c_p$, and thermal conductivity, k, by providing simple techniques which allow accurate determination of both properties is a sample of interest using a single sensing system. The present invention comtemplates generating an energy or temperature pulse in one or more heater elements disposed in and closely coupled to the fluid medium (gas or liquid) of interest. Characteristic values of k and $c_p$ of the fluid of interest then cause corresponding changes in the time variable temperature response of the heater to the pulse. Under relatively static sample flow conditions this, in turn, induces corresponding changes in the time-variable response of one or more temperature responsive sensor coupled to the heater principally via the fluid medium of interest.

The thermal pulse of a source need be only of sufficient duration that the heater achieves a substantially steady-state temperature for a short time. This pluse produces both steady-state and transient conditions at the sensor. Thermal conductivity, k and specific heat, $c_p$, can be sensed within the same sensed thermal pulse by using the steady-state temperature plateau to determine k which is then used with the rate of change of temperature in the transient condition to determine $c_p$.

BRIEF DESCRIPTION OF THE DRAWINGS

FIG. 13 is a graphical representation of thermal conductivity determination based on the bridge output of FIG. 9(a ).

FIG. 14 is a theroetical graphical representation of sensor heat-up time versus pressure for several gases using the sensor configuration of FIG. 7b.

FIG. 17 is a graphical representation of sensor cooling time versus pressure for serveral gases using the sensor configuration of FIG. 7c.

DETAILED DESCRIPTION

The present invention, then, is directed to a system which enables both the determination of specific heat, $c_p$, and thermal conductivity, k. The system utilizes a thermal pulse approach which is based on generating an energy or temperature pulse in a heater, which is coupled to a sensor primarily by the fluid medium (gas or liquid) of interest. Both quantities can be determined from a single pulse.

Figure 6:
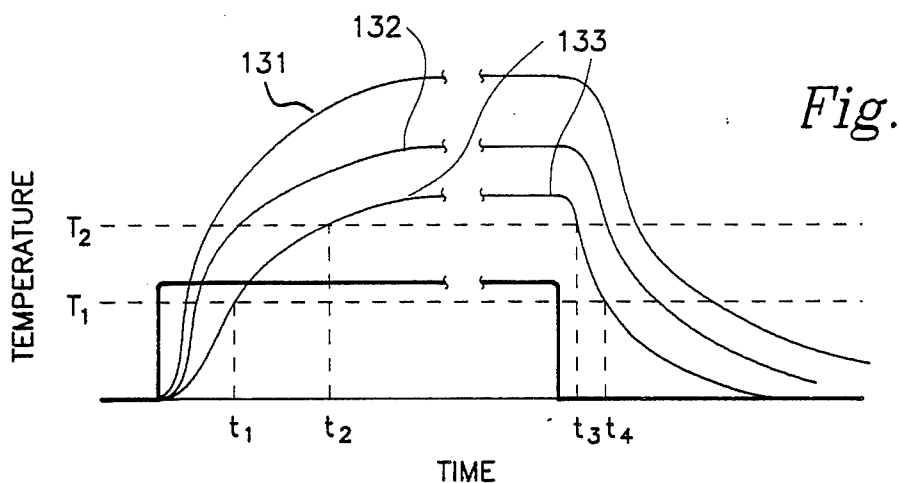
FIG. 6 is a schematic representation of sensor time-/temperature response curves according to a heater pulse.

Thermal conductivity and specific heat of each fluid of interest produce characteristic transient and steady-state temperature reactions in a proximate sensor as exemplified in FIG. 6.

In the preferred implementation, specific temperatures, as $T_1$ and $T_2$ in FIG. 6, are selected as "marker" points with respect to the sensor. These marker points are used to reference the determination of the time periods, as $t_1-t_2$, required to achieve the corresponding temperature rise(s) or fall(s) in the sensor(s) between the marker points. As will be discussed, the sensor or sensors are located in predetermined spaced relation to the heater or heaters, but preferably physically separated therefrom so that the proximate influence of the solid heater material(s) is reduced and the coupling of the heater with the sensor or sensors by the fluid of interest is relatively enhanced.

The preferred embodiments of the approach of the invention contemplate disposing spaced microscopic sized heating and sensing elements in a relatively static (zero flow) sample of the fluid of interest. The microsensor system or "microbridge" system, as it will be referred to herein, though not limiting, is presently preferred for several reasons. The system is extremely fast reacting, is very accurate, very sensitive because of its advantageous coupling to the fluid of interest and small and adaptable to a variety of configurations.

The microbridge semiconductor chip sensor contemplated, for example, in certain embodiments preferred for the invention may resemble the form of one or more of the microbridge systems illustrated in the patents identified above. Such a system is exemplified by FIGS. 1-5 taken from Pat. No. 4,501,144. A discussion of that example will now be presented as it will be helpful in understanding the present invention. While the present discussion is believed sufficient, to the extent necessary, any additional material contained in the microbridge related patents cited is deemed to be incorporated herein by reference.

The illustrated embodiment of FIGS. 1-5 contemplates a pair of thin film temperature sensors 22 and 24, a thin film heater 26 and a base 20 supporting the sensors and heater out of contact with the base. Sensors 22 and 24 are disposed on opposite sides of heater 26. Body 20 is a semiconductor, preferably silicon, chosen because of its adaptability to precision etching techniques and ease of electronic chip producibility. The embodiment includes two identical temperature sensing resistor grids 22 and 24 acting as the thin film heat sensors and a centrally located heater resistor grid 26 acting as the thin film heater.

Figure 8:
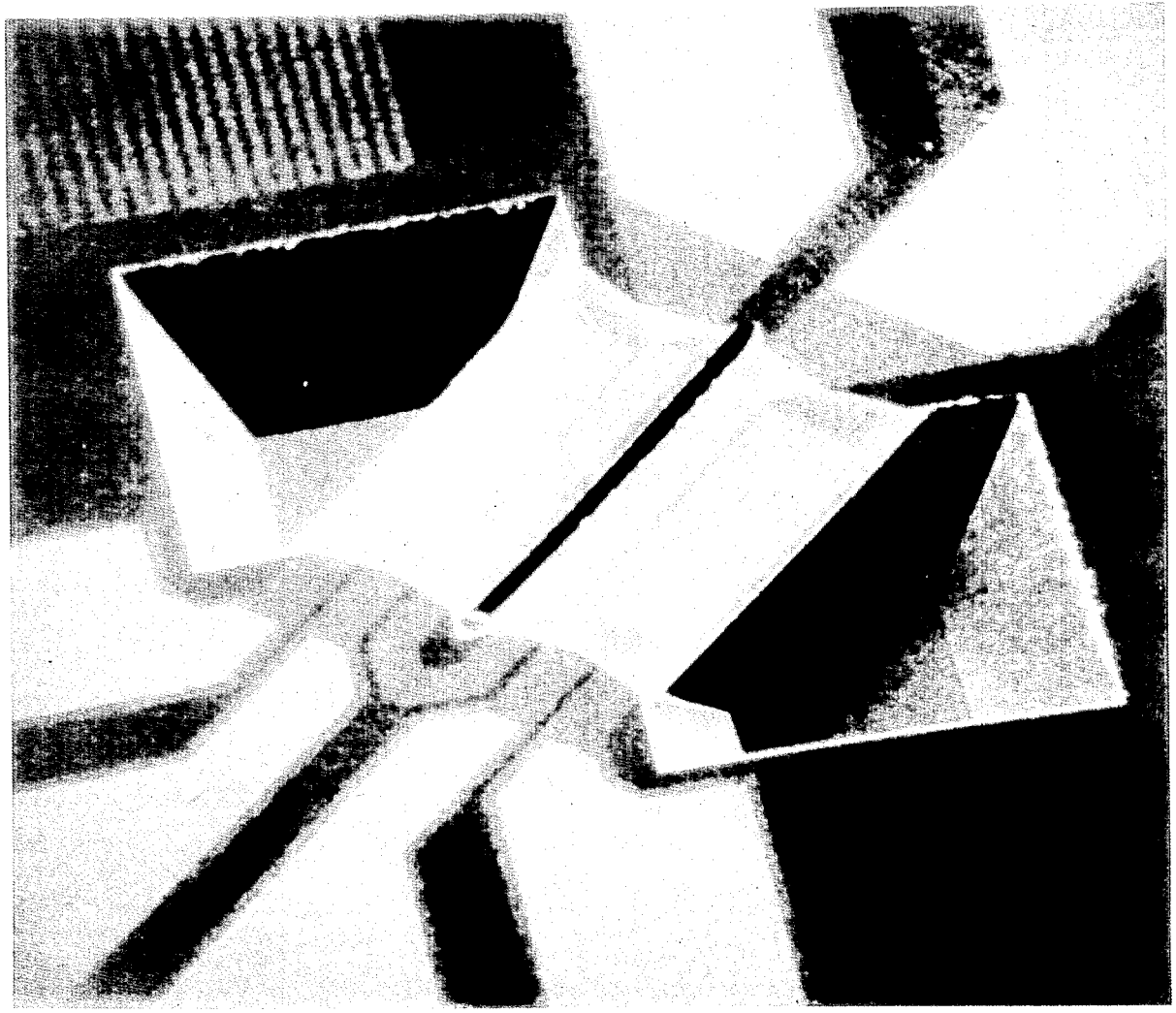
FIG. 8 is a scanning-electron-microscope (SEM) photo of the micorstructure of a typical microbridge sensor.

Sensors 22 and 24 and heater 26 may be fabricated of any suitable, stable metal or alloy film. In FIG. 8, the metal used was a nickel-iron alloy sometimes referred to as permalloy, with a composition of 80 percent nickel and 20 percent iron. The sensor and heater grids are encapsulated in a thin film of dielectric, typically comprising layers 28 and 29 and preferably silicon nitride, $Si_3N_4$, to form this film members. In the embodiment shown in FIGS. 1 and 2, the sensor comprises two thin film members 32 and 34, member 32 comprising sensor 22 and 34 comprising sensor 24, each member comprising one-half of heater 26 and having a preferred dimension of 150 microns wide and 400 microns long.

The embodiment of the system further describes an accurately defined air space 30 which contemplates air space effectively surrounding elements 22, 24, 26. The effectively surrounding air space is achieved by fabricating the structure on silicon surface 36, thin film elements 22, 24 and 26 having a preferred thickness of approximately 0.08 to 0.12 micron with lines on the order to 5 microns wide and spaces between lines on the order of 5 microns the elements encapsulated in a thin silicon nitride film preferably having a total thickness of approximately 0.8 microns or less, and by subsequently etching an accurately defined air space, of about 100 microns deep, into silicon body 20 beneath members 32 and 34.

Figure 1:
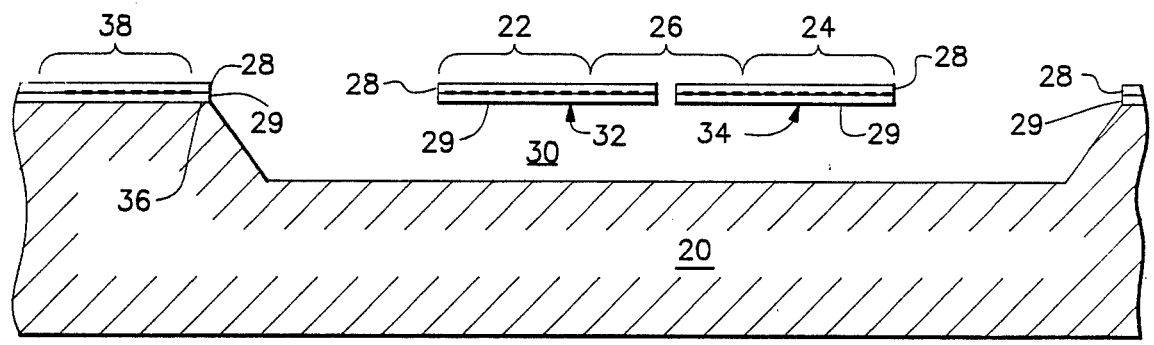
FIGS. 1, 2, and 3 are different views of a prior art embodiment of a microbridge flow sensor.
Figure 2:
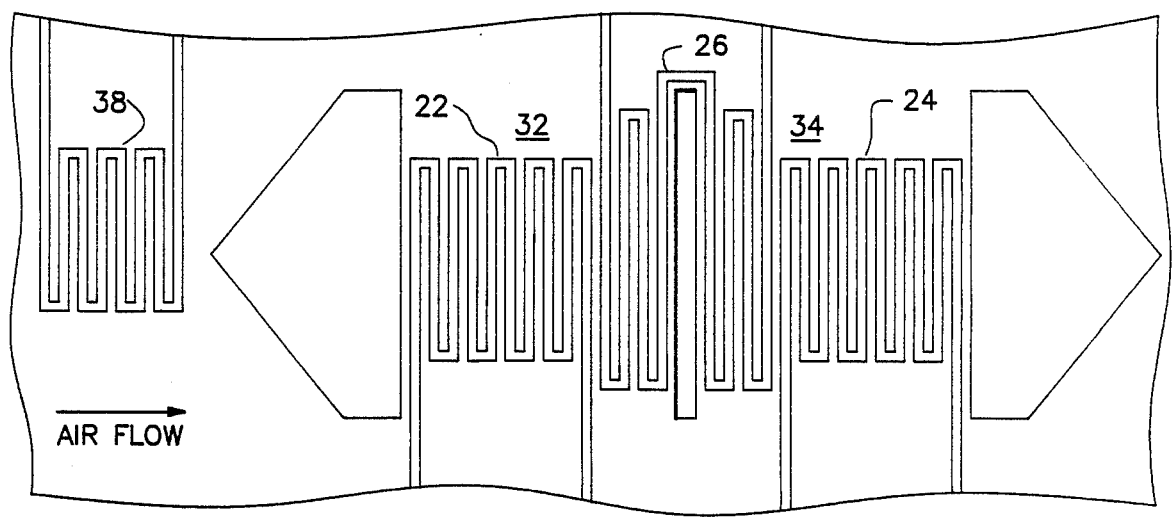
Figure 3:
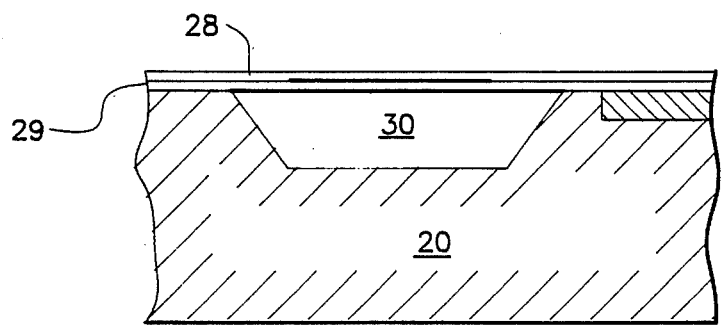
Figure 4:
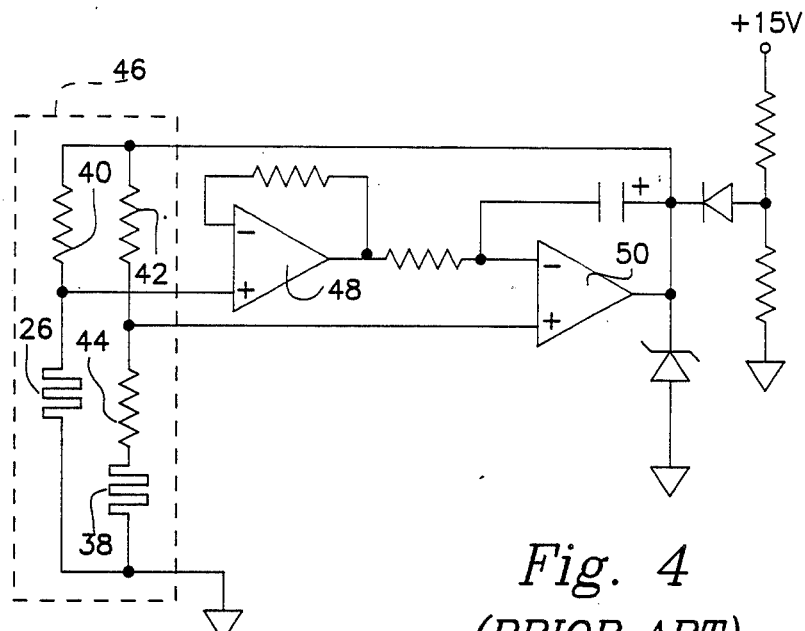
FIGS. 4 and 5 are typical circuits for use with the sensors of FIGS. 1-3.

Members 32 and 34 connect to top surface 36 of semiconductor body 20 at one or more edges of depression or air space 30. As illustrated in FIG. 3, members 32 and 34 may be bridged across depression 30; alternately, for example, members 32 and 34 could be cantilevered over depression 30.

Heat flows from the heater to the sensor by means of both solid and fluid couplings therebetween. Of note is the fact that silicon nitride ($Si_3N_4$) is a highly effective solid thermal insulator. Because the connecting silicon nitride film within members 32 and 34 is a good insulator, heat transmission through the solid does not dominate the propagation of heat from heater 26. This further enhances the relative amount of the heat conducted to sensing resistor 22 and 24 from heater resistor 26 by flow through the surrounding fluid rather than through the supporting nitride film. Moreover, the supporting silicon nitride film has a low enough thermal conductivity that sensing resistor grids 22 and 24 can be located immediately adjacent or juxtaposed to heating resistor grid 26. Thus, sensing resistor grids 22 and 24 are in effect suspended rigidly in the air space proximate heater resistor 26 and act as thermal probes to measure the temperature of the air near and in the plane of heater resistor grid 26.

The operation of the system in sensing air flow is described in detail in the above-referenced U.S. Pat. No. 4,501,144. Typical circuit implementation is discussed briefly with reference to FIGS. 4 and 5 to add some insight. The heater control circuit illustrated in FIGS. 4 uses a Wheatstone bridge 46 which further typically includes heater resistor 26 and a resistor 40 in its first leg and a resistor 42, heat sink resistor 38, and a resistor 44 in its second leg. An error integrator includes amplifiers 48 and 50 keeps bridge 46 balanced by varying the potential across it and thus the power dissipated in heater resistors 26.

Figure 5:
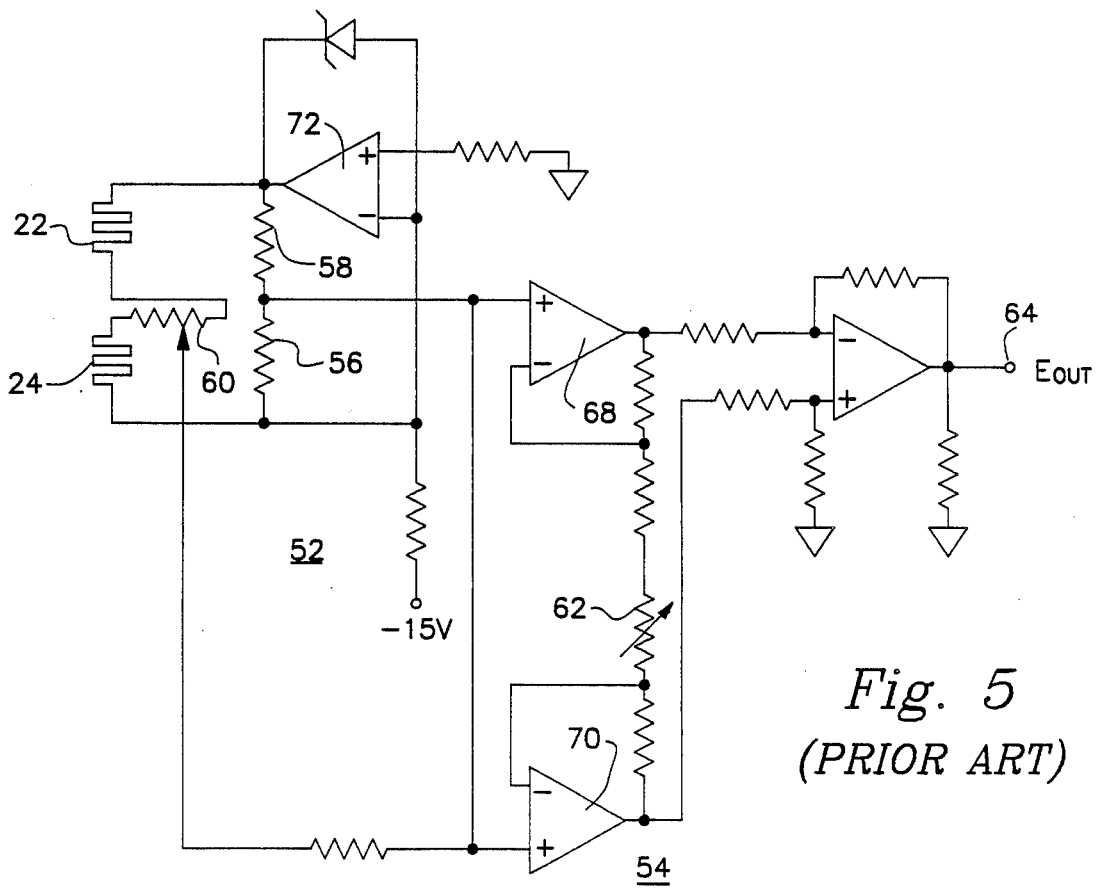

The circuitry of FIG. 5 monitors the resistance difference between downstream sensor 24 and upstream sensor 22. This circuitry includes a constant current source 52 comprising an amplifier 72 and a differential amplifier 54 further including amplifiers 68 and 70. The constant current source drives a Wheatstone bridge comprising two high impedance resistors 56 and 58 in one leg and the two sensing resistors 22 and 24 with a nulling potentiometer 60 in the other leg. The gain of differential amplifier 54 is adjusted by potentiometer 62. Output 64 provides an output voltage that is proportional to the resistance difference between the two sensing resistors 22 and 24.

To get some concept of the small size of the microbridge, the power required by heater resistor to heat such a device 200° C., for example, above ambient temperature is less than 0.010 watt. The exceedingly small thermal mass of the heater and sensor element structures, their excellent coupling to the surrounding fluid because of a high surface/volume ratio, and the thermal insulation provided by the thin silicon nitride connecting them to the supporting silicon body, and the surrounding air space, all contribute to produce a system well suited to fast and accurate sensing. Response time constants as short as 0.005 second have been measured. Consequently, sensor elements can respond very rapidly to proximate environmental changes.

Figure 7A:
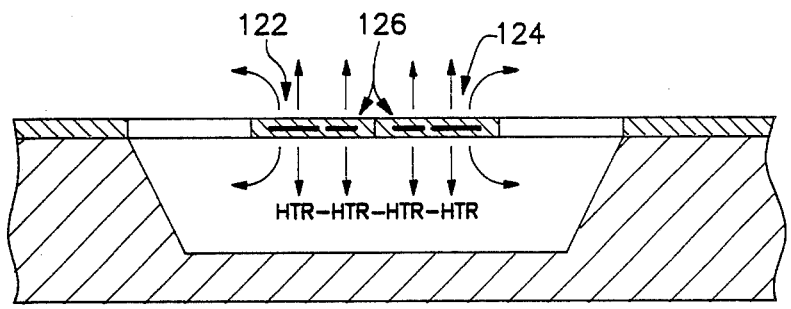
FIGS. 7a, 7b, and 7c, represent several heater/sensor configurations of microbridge systems in accordance with the invention.
Figure 7B:
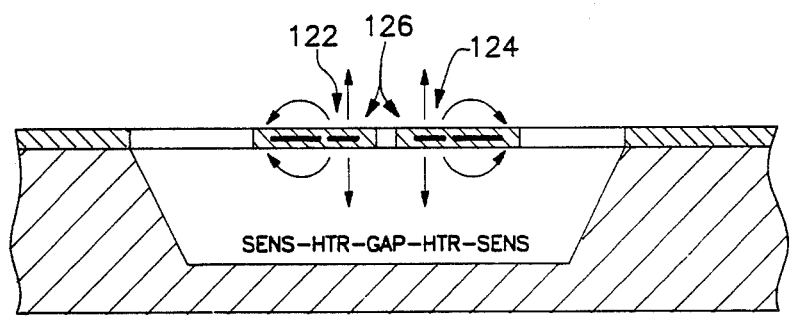
Figure 7C:
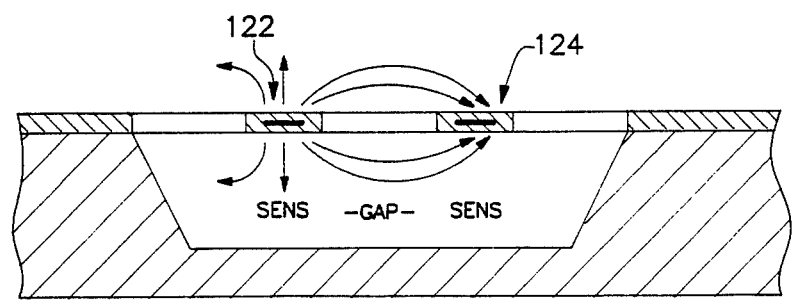

Now with reference to the implementation of the present invention, FIGS. 7a, 7b, and 7c, depict three slightly differing embodiments or configurations representative in terms of number and arrangement of the heaters and sensors which can be used in this invention. In FIG. 7a, in contrast to FIG. 1, all of the elements 122, 124 and 126 are used as heaters. FIG. 7b is an embodiment which is similar to the embodiment of FIG. 1 with thin film element 126 acting as heater and elements 122 and 124 acting as sensors. The embodiment of FIG. 7c, represents the preferred arrangement in which the element 122 acts as heater and element 124 acts as sensor. The effective gap and thus the thermal isolation between heater and sensor is desirably wider in the embodiment of FIG. 7c.

The actual general geometric structure of the embodiments of FIGS. 1-3, and 7a-7c is more clearly illustrated in the scanning electron micrograph (SEM) photo to FIG. 8. The precision with which the cavity and bridge elements are defined and located in spaced relation, as FIG. 8 depicts, is particularly noteworthy. The SEM represents a magnification such that the indicated length of 0.010" appears as shown.

In the implementation of the invention disclosed herein particular attention is directed to (1) setting specific temperature markers in the sensor to determine the time periods needed for achieving the corresponding temperature changes, (2) using temperature sensors which are physically separated from the heater so that the direct influence of the heater and heat conducted to the sensor other than via the fluid of interest is reduced, and (3) using a pulse which reaches at least a momentary steady-state plateau to determine k, which then is used with the transient measure to determine $c_p$.

Figures 11, 12:
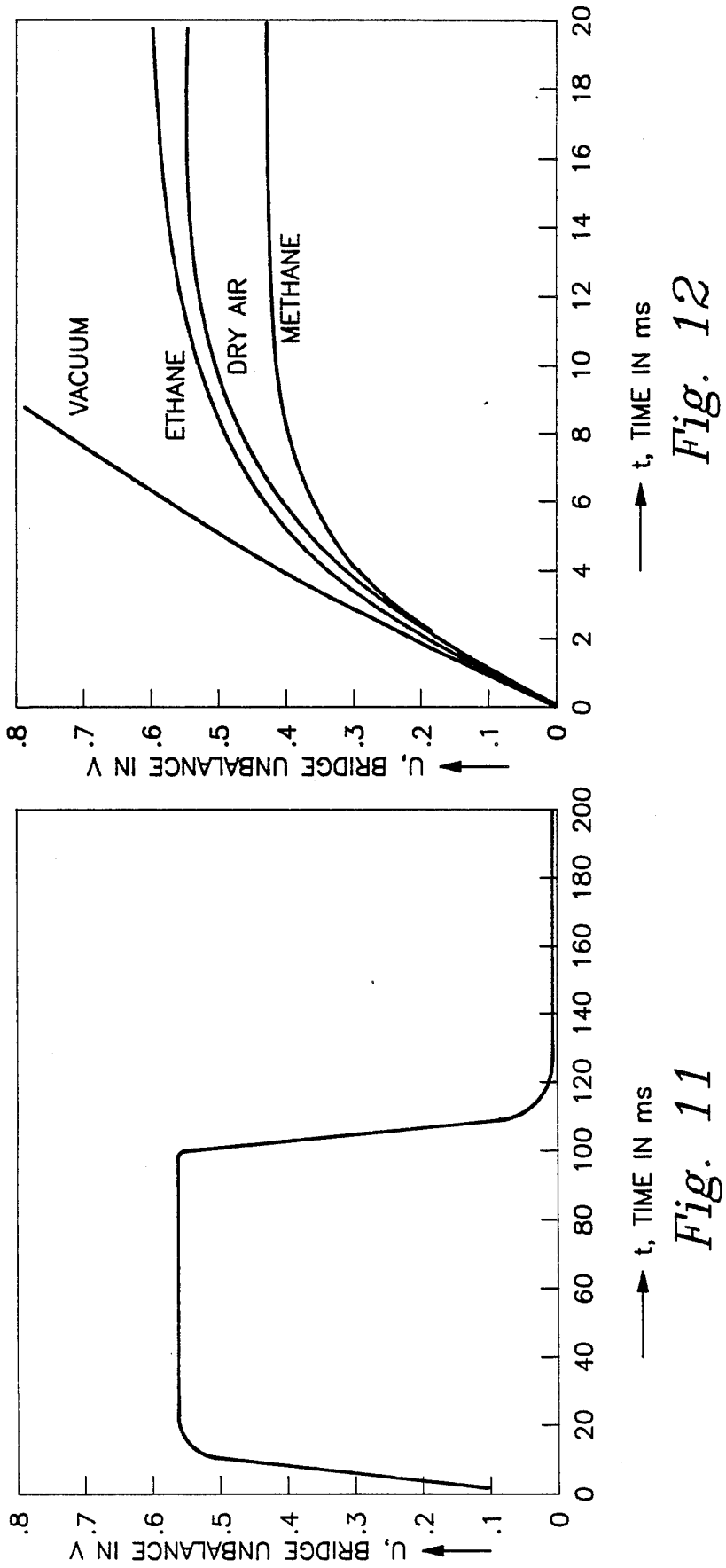
FIG. 11 us a scope trace representing the temperature signal rise versus time, for the configuration of FIG. 7(c) in response to a heater pulse for dry air at atmospheric pressure.
FIG. 12 is a graphical representation of the temperature signal rise versus time, for the configuration of FIG. 7(c) in respnse to the heater pulse for various gases at atmospheric pressure as indicated.

FIG. 6 graphically depicts a square wave electrical energy pulse 130 to the heater as at 126 which results in quasi square wave heat pulses released by the heater. These in turn, result in reactive curves as at 131, 132 and 133 at the sensor which vary as described below. The pulse applied to the heater, for example, may have a height of about 4 volts with a pulse width of 100 ms. Since the heater is closely coupled through the fluid medium to the sensors, the family of curves 131, 132 and 133 resembles the shape of the input pulse. They show the heat response in the sensors 122 and 124. FIG. 11 represents an oscilloscope trace showing temperature rise and fall versus time for dry air at atmospheric pressure. The configuration is that of FIG. 7b with a heater resistance of 800 ohms at room temperature, a heater pulse height of 2.5 volts and a heater pulse width of 100 ms. It uses a different scale for time than does FIG. 6, but illustrates the curve form produced by the pulsed input. The curves generally include beginning and ending transient portions flanking a relatively steady-state central portion. The relatively quick response of the sensor allows a relatively long steady-state to exist even with a pulse of 100 ms. Of course, the curves are affected by factors such as pressure and temperature as they influence the effective thermal conductivity and specific heat of the particular fluid of interest.

Heat flowing from the heater element or elements to the sensor element or elements is conducted both through the fluid and through the solid semiconductor element support substrate or the like. It is advantageous with respect to the measurement of k or $c_p$ of the fluid of interest that the amount of heat reaching the sensor through the solid connections be minimized so that substantially all the measured thermal effect is generated via the fluid of interest.

With respect to the transfer of heat to the sensor(s) some background information regarding the propagation of heat or temperature waves is presented. The speed of progation, v, of a one dimensional wave (if it features an exponential decay profile) is constant and given by the expression:

$$v = D_T/a = (D_T/b)^{0.5}, \qquad (1)$$

where:
 a is an exponential decay constant
 b is the rise time constant at a fixed location and
 $D_T$ is the thermal diffusivity.

A complete list of nomenclature and subscripts with units appears in Table I, below. $D_T$ is related to k and $c_p$ by the expression $$D_T = k/c_p \qquad (2)$$

$D_T$, therefore, if known, may be a key to obtaining $c_p$. The rise time constant, b, was measured to be about 4 msec. For typical gases, $D_T$ ranges from 1.7 cm²/s for He to 0.054 cm²/s for $C_3H_8$. Metals exhibit high values such as 1.7, 1.1 and 0.18 cm²/s respectively for Ag, Cu and Fe. Insulators, however, are even lower than the gases at 0.004 cm²/s for glass and 0.0068 cm² for $Si_3N_4$ which, as discussed above, is a good insulator. The propagation speed, v, in a typical gas sample then is about $(1/0.004)^{0.5} = 15$ cm/s. This compares with $(0.0068/0.004)^{0.5} = 1.3$ cm/s for $Si_3N_4$, assuming that the same rise time constant of about 4 ms is applicable to both the one measured in the $Si_3N_4$ and the actual one in the gas.

The effect is that the influence of the temperature wave propagating from one thin film strip, that is, the heater, to a second thin film strip, the sensor, both being embedded in a membrane of $Si_3N_4$, is faster for the gas than for the $Si_3N_4$. This also supports the choice of a material such as $Si_3N_4$, since it reduces the contribution of heat flow through the solid media. This is beneficial to the accuracy of the system.

Typical microbridge embodiments are illustrated by FIGS. 7a-7c. They will now be explained in greater detail.

TABLE I

| Symbol | | Units |
|---|---|---|
| | NOMENCLATURE | |
| $a$ | Exponential Decay Constant | cm |
| $a_1$–$a_n$ | Constant | |
| A | Area of Heat Transfer to Microbridge or to Gas | cm$^2$ |
| b | Rise Time Constant at a Fixed Location | °C./s |
| $c_p$ | Specific Heat | cal/(cm$^3$ °C.) |
| $D_T$ | Thermal Diffusivity, $D_T = k/c_p$ | cm$^2$/s |
| k | Thermal Conductivity | cal/(sm °C.) |
| L | Length of Thermal Conductance Path in Gas or Solid | cm |
| P | Pressure of Gas | psia |
| Q | Power of Heat Release Rate | watts |
| $R_o$ | Resistance at Room Temperature | ohms |
| t | Time | s |
| T | Absolute Temperature | °C. |
| U | Bridge Output or Amplified Bridge Output | V |
| V | Volume of Gas or Solid (Microbridge) | cm$^3$ |
| v | Speed of Propagation | cm/s |
| x | Temperature coefficient of resistance | °C.$^{-1}$ |
| | SUBSCRIPTS | |
| c | Conduction | |
| S | Microbridge or Solid | |
| g | Gas | |
| o | Room, Reference or Gas Temperature Without Microbridge Heating | |
| h | Heater or Hot | |
| m | Middle or Medium | |

The configuration of FIG. 7a involves using the same microresistance 122, 124, 126 for the heating pulse and the sensing task. In this embodiment of the resistive heater-sensor element may be one leg of a conventional resistive Wheatstone bridge in a control circuit.

FIG. 7b depicts an arrangement wherein the center microresistance structure 126 is used as a heater flanked by two symmetrically located outer sensing resistance elements 122 and 124. The elements 122 and 124 are separated from the heater 126 by a narrow gap.

FIG. 7(c) shows an embodiment configuration in which the left element of the bridge 122 is used as the heating element and the right element 124 as the sensor. This embodiment takes advantage of a rather large central gap to achieve improved thermal isolation between the heater and the sensor.

Figure 9:
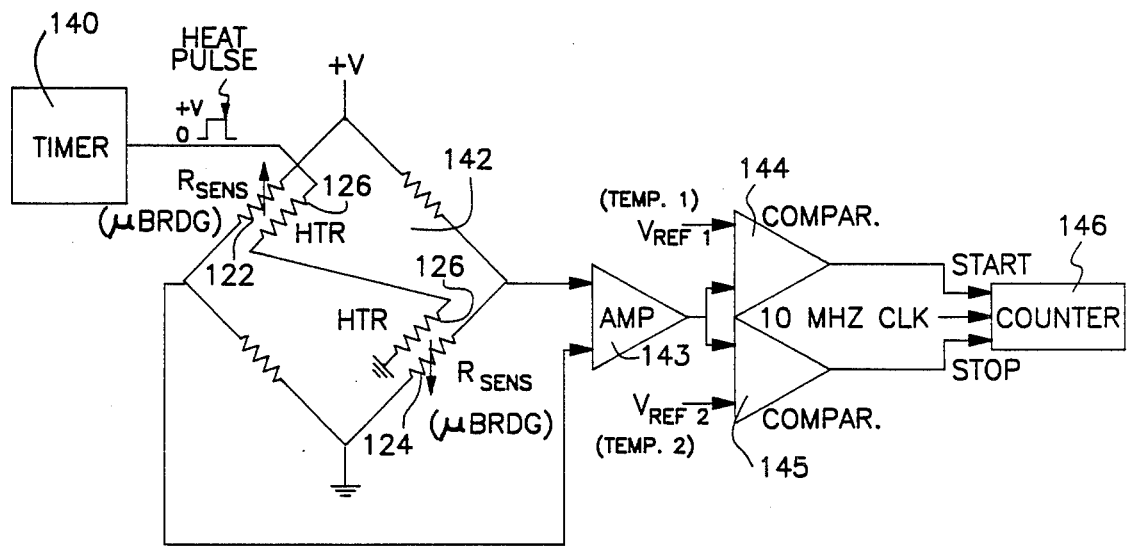
FIG. 9 is a partial schematic and block diagram of a circuit for use with sensor as depicted in FIG. 7(b) in accordance with the invention.

FIG. 9 shows a modified control circuit which uses the center microresistance 126 as heater, while the sensing task is performed by the two resistors 122 and 124. The dual heater sensor configuration corresponds to FIG. 7b and the circuit is representative of typical sensor/measurement circuit. FIG. 9 includes a timer 140 providing square-wave electrical pulses to the heater 126. The heater couples the heat pulse to the sensors 122 and 124 in the bridge 142. The output of the bridge is connected through an amplifier 143 to a pair of comparators 144 and 145 which operate "start" and "stop" inputs to a counter 146 which counts 10 mHz clock pulses. The counter counts measure the time interval $(t_2-t_1)$ between temperatures $T_2$ and $T_1$ illustrated in FIG. 6.

Figure 9A:
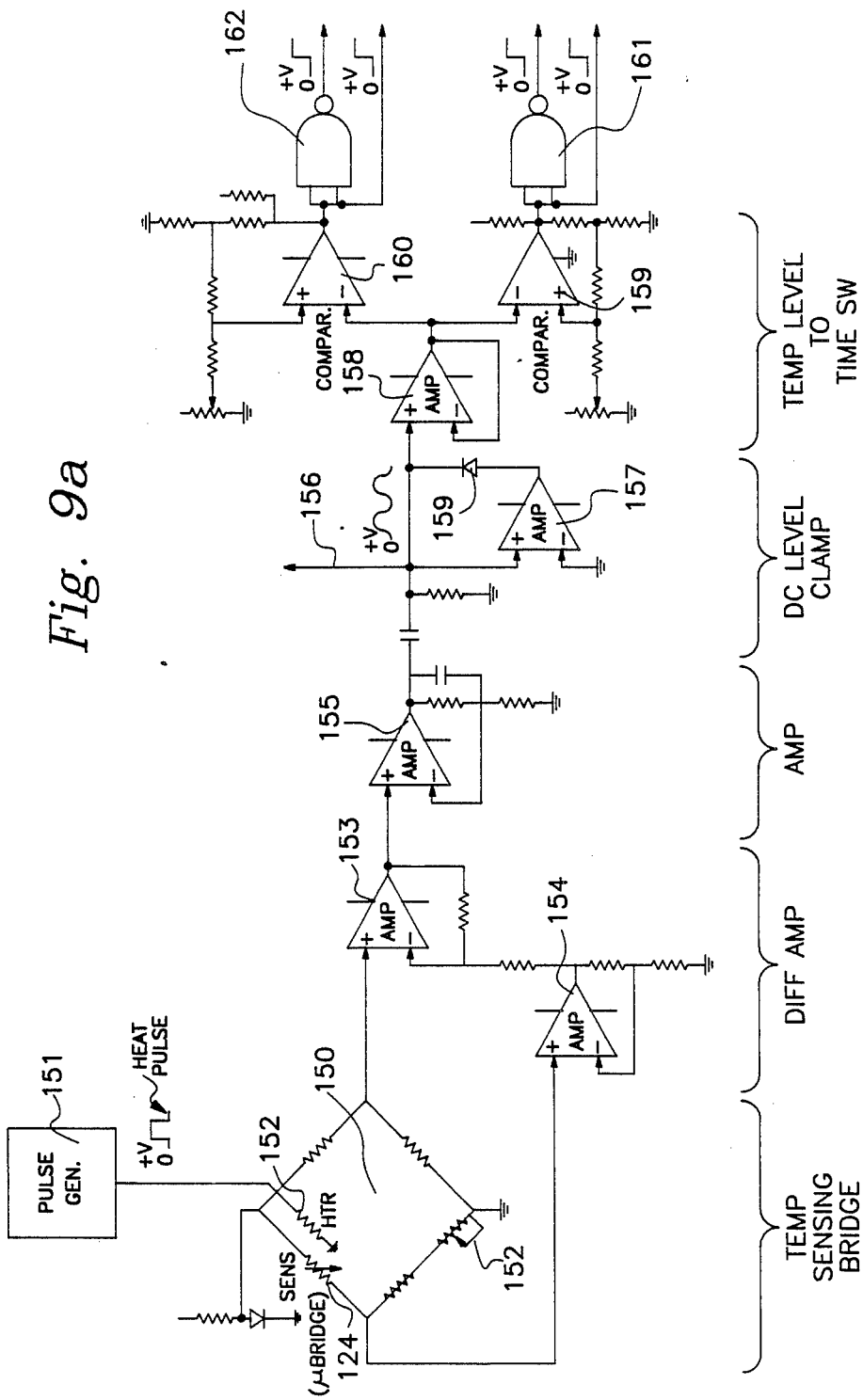
FIG. 9a is a more detailed circuit schematic with reference to FIG. 7c.

FIG. 9a is similar to FIG. 9, but more detailed. The bridge configuration is the heater-space-sensor configuration of FIG. 7c. The sensor resistance arm of the microbridge is set into a Wheatstone bridge 150 at 124. Another proximate resistive arm 122 is fed a voltage pulse from pulse generator 151 to provide a heat pulse into the microbridge element 126. The Wheatstone bridge 150 also may contain a nulling balancing resistor 152 which can be used in the manner of potentiometer 60 in FIG. 5 to initially zero the device. The microbridge resistor sensor 124 in the Wheatstone bridge receives the heat pulse from heater element 122 principally by thermal conduction through the surrounding fluid. Some conduction, of course, does occur through the solid microbridge substrate and surroundings.

The circuitry of FIG. 9a is conventional and can readily be explained with reference to its functional operation with regard to processing the bridge output signal. The voltage output signals of the bridge 150 are amplified by differential amplifiers 153 and 154 in a differential amplifier section. The imbalance signal is further amplified by a high gain amplifier at 155. The signal at 156 as is the case with the signal at 147 in FIG. 9 is in the form of a DC voltage signal, U, the amplitude of which is solely related to the thermal conductivity of the fluid of interest as will be discussed above.

The remainder of the circuitry of FIG. 9a includes a DC level clamping amplifier 157 and isolation amplifier 158. The temperature level, time-related switching and counting circuitry includes comparators 159 and 160 together with Nand gates 161 and 162 having outputs which are connected to the counter timing device (not shown) as in FIG. 9. By measuring the time needed for the sensor temperature to rise or fall between two or more known temperature values or markers as represented by sensor resistance or bridge voltage outputs a measure related to the specific heat per unit volume, $c_p$ of the fluid of interest is obtained. The timing device may be a conventional 10 MHz pulse counter or the like. Again, this is illustrated schematically in FIG. 6.

The output signal from the Wheatstone bridge, U, represents the voltage imbalance caused by the temperature change in microbridge sensor or sensors induced by the corresponding heater pulse output. Because the magnitude of this imbalance is related directly to the amount of energy absorbed by the sensor or sensors, the amplitude of the signal is directly related to the thermal conductivity, k, of the conducting media in a manner next explained.

FIG. 6 shows that during much of the about 100 ms wide pulse period the temperature of the sensor reaches and maintains a constant value. During this time, the influence of the energy sink or source terms represented by specific heat are zero, which means that only thermal conductivity governs the value of the sensor temperature.

FIG. 12 is a plot of temperature rise in the form of bridge output, U, (FIG. 9 or 9a) using the sensing arrangement of FIG. 7(b) versus time in milliseconds for various gases at atmospheric pressure. Curves for methane, dry air, ethane and a vacuum are presented. In this specific embodiment there was a heater resistance of 800 ohms, a pulse height of 2.5 volts, and a pulse width of 100 ms. Temperature markers t, and $t_2$ are shown on the graph. These markers relate to those of FIG. 13 which shows a graphical presentation of heat up time versus pressure for several gases with a sensor-heater such as that shown in FIG. 7b and using the $T_2-T_1$, marked in FIG. 11.

The literature value of the thermal conductivity of several gases has been plotted vs. the measured sensor temperature expressed directly in terms of the measured Wheatstone bridge imbalance potential, U. This relationship has been derived empirically for a microbridge of the type depicted in FIG. 7(c) and is plotted in FIG. 13, using the least squares method in a multiple regression analysis to achieve the best fit curve. The relation can be linearized over a modest span sufficient for the purpose of the invention. Other combination configurations of heater/sensor embodiments can likewise be calibrated using known gases or gases of known k. Thus, using an off-the-shelf flow sensor of the type 7(c) in the circuit 9(a), a 4.0 V pulse of 100 ms duration was used.

This yielded an approximate linear relationship between U and $k_g$ of the form $$k_g = a_4 U + a_5 \tag{3}$$

where $a_4 = -25.8807$ and $a_5 = 181.778$ for the above conditions.

The above then achieves the calibration of the sensor for $k_g$. The linear approximation holds over enough of a span to provide accurate measurements. Similar relations may be derived under other measurement conditions including additional pressure correction terms.

Further details related to determinng the coefficients for the algorithms to compute $c_p$ are described next. This determination requrires that the measuring system be calibrated first, which consists of determining the coefficients $a_1$, $a_2$, and $a_3$, of the algorithm to then compute $c_p$.

Assuming a two-dimensional model for heat transfer in the microbridge, see FIGS. 7a–7c, the measured sensor temperature response may be described with reference to the following processes (at zero gas flow):

(1) Heat release by the heater element film.
(2) Temperature build up in the heater element material (FeNi or Pt) and surrounding support material (insulator $Si_3N_4$), i.e. within the bridge material.
(3) Conduction towards the sensor via (a) the bridge material, and (b) the fluid phase surrounding the bridge.
(4) Temperature build up in the sensor material (as in heater material in item 2 above), and in the gas surrounding it by the heat arriving via the above processes.
(5) Achieving a steady-state distribution of temperature.
(6) The revenue process to steps 1–5 during the start of the heater off-period.

Further assuming, for the sake of simplicity, that the specific heats of the involved gaseous and solid materials do not depend on temperature, we can approximately describe the above processes by the following expressions (see Table I above for symbol explanation) using the same process numbering as above:

(1) $Q = V^2/(R_o(1 + a(T_h - T_o)))$ for small temperature rises.
(2) The heater temperature results from balancing the heat input and output rates: $T_h - T_o = Q/(k_s A_s/L_s + k_g A_g/L_g)$ with Q in watts; the temperature $T_h$ is established in a time that is short compared to the time it takes to reach the sensor if the sensor is not identical to the heater, as in configurations 7(b) and 7(c).
(3) In a truly one-dimensional case most of 50% of the released power Q eventually arrives at the sensor, since it only has two ways to go ($+x$ and $-x$ directions). In a two- (or even three-) dimensional case a major part of Q gets dissipated in the y and z directions, so that only a fraction, $Q_c$, is conducted to the sensor, with a corresponding drop of the original temperature, $T_h$, down to an intermediate temperature $T_m$. The sensor then experiences an energy rate arrival of $$Q_c = (T_m - T_o)(k_s A_s/L_s + k_g A_g/L_g) \tag{4}$$

(4) The sensor temperature rise rate is governed by the specific heat of the gas surrounding the sensor and the closely coupled material of the sensor itself so that:

$$Q_c = (dT/dt)c_{ps}V_s + (dT/dt)c_{pg}V_g \tag{5}$$

Figure 16:
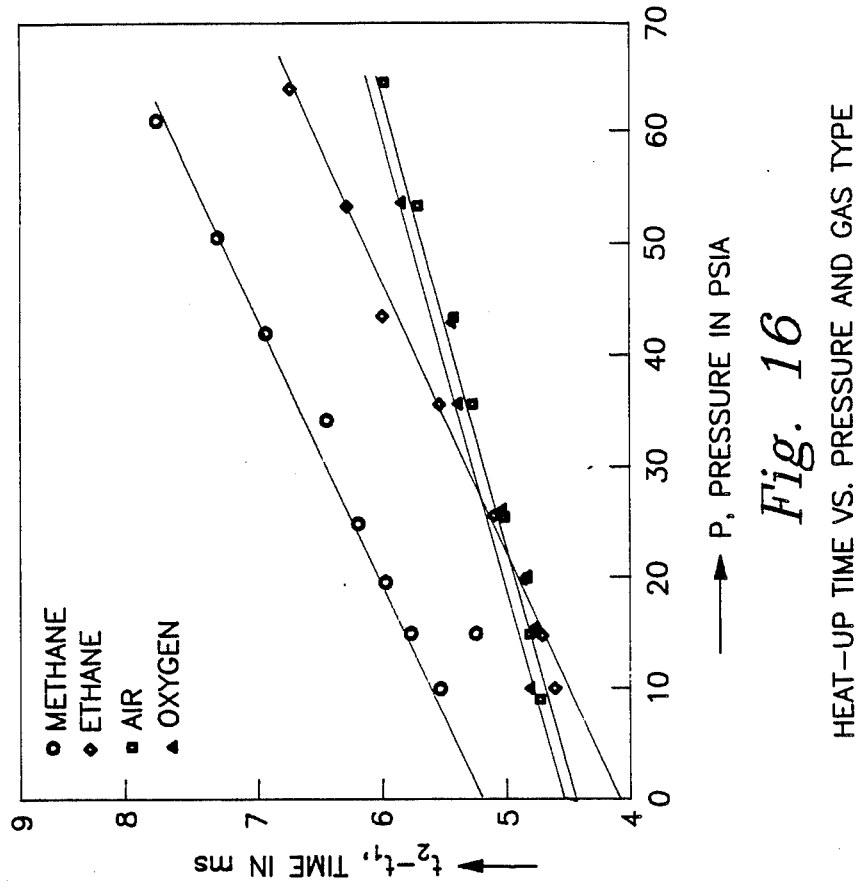
FIG. 16 is a graphical representation of sensor heat-up time versus pressure for several gases using the sensor configuration of FIG. 7c.
Figure 15:
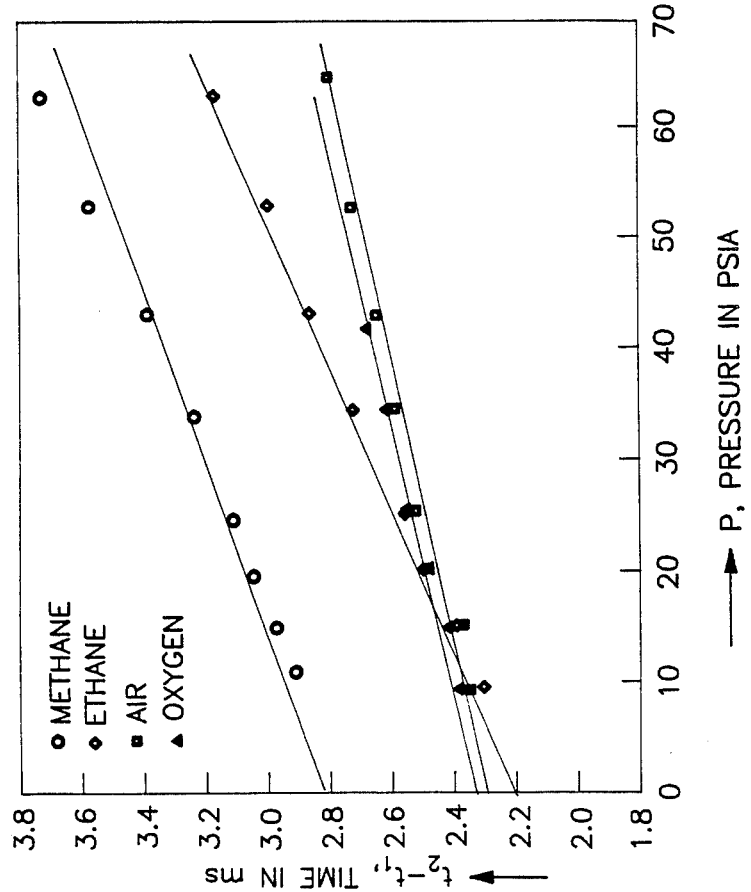
FIG. 15 is similar to FIG. 14 based on data taken by a sensor of the type depicted in FIG. 7(b) calculated in accordance with the invention.

The quantity measured and plotted in FIGS. 14, 15 and 16, is the time (dt) needed to raise the sensor temperature by an increment (dT) which is chosen by the two or more sensor resistance value markers corresponding to $T_1$ and $T_2$. FIG. 14 and FIG. 15 are for configuration 7b with a pulse height of 2.5 volts and a pulse width of 100 ms. FIG. 16 is for configuration 7c with a pulse height of 1.75 v. and a pulse width of 100 ms.

It is readily apparent from equation (5) that $c_{pg}$ could be determined for an unknown gas if the various quantities entering in Eqs. (4) and (5) were either known or measurable. It has been found, however, that even if only dt, dT, $T_o$, P and $k_g$ are conveniently measurable, the other quantities may be determined by calibration. This can be done according to an invention as follows:

For calibration, gases of known composition (preferably but not necessarily pure) and therefore of known specific heat and thermal conductivity at the used pressure and temperature (both also measured), are brought in contact with the sensor. The effect of the pulsed heat releases is recorded in terms of the lapsed time, $t_2 - t_1$, as has been described. After noting results for various gases, pressures, heater temperatures and/or heating-/cooling periods, with pulses of constant temperature, voltage, current or power, the recorded time and condition data are entered into an array of data ports which can be used for automatic or computerized data processing or other number crunching techniques.

The process can be illustrated with the help of equations (4) and (5), by way of example, without excluding other, similar approaches likely to occur to one skilled in numerical analysis. With this in mind, the following ports receive data or input for various gases, pressures (and temperatures):

| Ports: | Y | X1 | X2 |
|---|---|---|---|
| Inputs: | $c_{pg}P/P_o$ | $(t_2-t_1)k_g$ | $t_2-t_1$ |

Known and available multiple linear regression analysis (MLRA, see FIG. 10) program can determine the linear coefficients, $a_1$, $a_2$, and $a_3$ (e.g., by matrix inversion), which, together with the above input data, forms the calibrated expression derived from equations (4) and (5) to compute specific heat, $c_p$:

$$c_{pg}P/P_o = a_1(t_2-t_1)k_g + a_2(t_2-t_1) - a_3 \tag{6}$$

The determined (calibration) coefficients, or course, represent the lumped factors of several sensor properties or conditions from equations (6) and (7):

$$a_1 = (T_m - T_o)(A_g/L_g)/(V_g dT), \tag{7}$$

$$a_2 = (T_m - T_o)(A_g/L_s)/(V_g dT)k_s,$$

-continued $$a_3 = c_{ps}V_s/V_g$$

In order to minimize differences in $T_m$ at the sensor location, the most advantageous operation from among constant temperature, voltage, current or power is chosen. The above method is demonstrated on the basis of (1) constant voltage pulses, which result in quasi square wave heat pulses released by the heater, and (2) changes in gas type ($CH_4$, $C_2H_6$, air and $O_2$) and pressure; the chosen configuration was 7(b).

FIG. 14 shows the result of storing and plotting the $dt=t_2-t_1$ and pressure data for each of the gases used, for which the $c_p$ and k values can be obtained from the open literature. This relation is linearized by applying the least squares method in a multiple linear regression analysis to achieve the best fit line. After entering these data into the above ports Y, X1 and X2, the regression analysis program performed. The obtained result was, for a configuration as in Figure 7(b):

$$a_1 = -16509, a_2 = 3.5184 \text{ and } a_3 = 0.005392 \quad (7a)$$

Proof that the above calibration coefficients are valid is provided by FIG. 15, for example, in which these coefficients have been used to generate the shown lines for $CH_4$, $C_2H_6$, air and $O_2$. As shown, the lines indeed connect and agree with all experimental points. Additional lines have been plotted with the $c_p$ and k data of the literature for other gases as well.

The final step in using this calibration method involves known means to store, write or burn in the obtained, tailored values of $a_1$, $a_2$ and $a_3$ for the individual microbridge, which may be a Honeywell MICROSWITCH Model No. AWM-2100V, into the memory linked to it. The microsensor is then ready for use to measure the specific heat of unknown gases, provided that P and k be known at the time of measurement.

Figure 10:
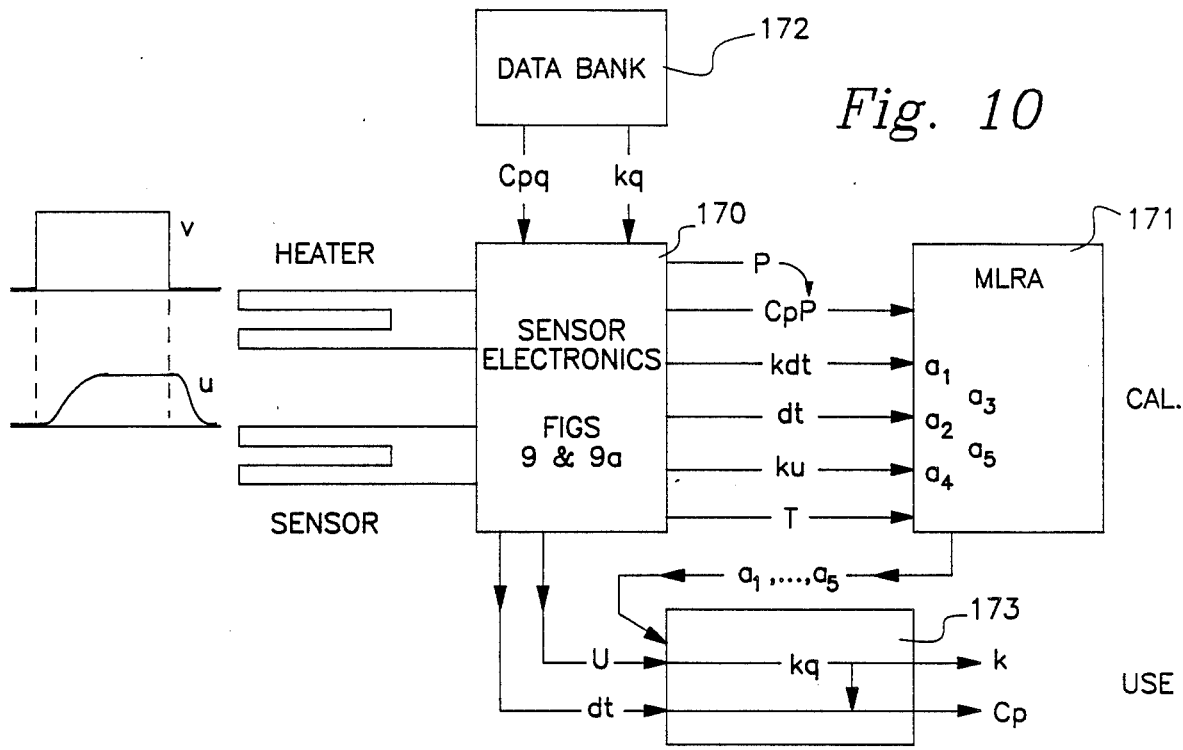
FIG. 10 is a schematic block diagram of the system of the invention including calibration and use functions.

FIG. 10 depicts a schematic block diagram of a device for measuring $c_p$ and k. The system includes the signal processing circuitry indicated by 170, a multiple linear regression analysis (MLRA) unit 171 for deriving the known equation constants for the particular microbridge configuration and circuitry used, i.e., $a_1 - a_n$, a data bank 172 for storing calibration $c_p$ and k data and an output interface unit 173.

With respect to the embodiment of FIG. 10, prior to use, field recalibration may be accomplished simply by entering the P, $c_p$ and k values of the test gas into the data bank. IF P cannot be measured independently of the sensor already in the subject system its errors can be incorporated as a correction in the $c_p$ and k recalibration. The measured values of U and dt are then used as in the measurement mode to determine sensor values of k and $c_p$. If they disagree from the entered values the constants $a_3$ and $a_5$ may be modified to fit the entered or book values.

This approach may be a practical one for field use, but it should be checked by using a second test gas. If that agrees, the recalibration may be completed. If not, a complete calibration of all $a_1$-$a_5$ coefficients should be made.

It should be mentioned that in all of the above discussion the influence of temperature was not mentioned for the sake of simplicity. It is well known, however, that temperature does influence both $c_p$ and k but can be addressed, if necessary, in one of the following ways:

(1) Controlled, (expensive and energy consuming) or
(2) Compensated by special temperature-sensitive elements in the analog part of the circuit, or
(3) Entered into the sensor algorithm as an additional parameter, which is sensed, e.g., by monitoring one of the many available temperature dependent resistors on the sensor. This is the preferred approach for sensing systems requiring maximum accuracy.

With respect to use of the instrument of FIG. 10, the U and $dt=t_2-t_1$ (and P) signals obtained for an unknown gas are processed as follows in this mode:

(1) Computation of k from expression (3) using the coefficients $a_4$ and $a_5$ which have been stored in (or burned into) the sensor's memory after calibration, and
(2) Computation of $c_p$ from expression (6). It should also be noted that a pressure signal is also needed as a basic ingredient since $c_p$ is used here in relation to a volume of gas as opposed to k which is largely pressure independent if the sensor is used at or above atmospheric pressure, at which the gas mean free path is small compared to the characteristic dimensions of the involved sensor.

The graphical presentation of FIG. 16 depicts heating time in milliseconds versus pressure and gas type and specifically showing curves for methane, ethane, air and oxygen. The sensing configuration of FIG. 7(c) was used. In this example, the pulse height was 1.75 volts with a pulse width of 100 ms. and the heater and sensor resistance each being about 2000 ohms. FIG. 17 depicts a cooling curve for the same configuration as FIG. 16. FIG. 17 is a plot of the cooling time vs. pressure for different types of gas. Conditions were the same except that the pulse height was 4.0 volts.

Of course, the output of the device can be in any desired form including analog or digital signals, printed records, etc., after the value is obtained.

We claim:

1. Apparatus for determining thermal conductivity, k, and specific heat, $c_p$, of a fluid of interest comprising;
   heater means;
   thermal sensor means in proximate position to said heater means and in thermal communication therewith through the fluid of interest, said sensor means being one having a temperature dependent output;
   adjustable energizing means connected to said heater means for energizing said heater means on a pulsed time-variable basis in a manner to induce both transient and substantially steady-state elevated temperature condition intervals in said thermal sensor means;
   first output means for providing first output signal indicative of the temperature of said thermal sensor means;
   means for determining the rate of change of temperature of said temperature sensor during a transient temperature interval based on time variation of said first output signal;
   means for detemining k of the fluid of interest based upon the first output signal at steady-state elevated sensor temperature; and
   means for determining $C_p$, of the fluid of interest based on k and the rate of change of the first output during a transient temperature condition.

2. Apparatus for determining thermal conductivity, k, and specific heat, $c_p$, of a gaseous fluid of interest, comprising:
   a microbridge system including a thin film resistive heater portion and a thin film resistive sensor portion in juxtaposed spaced relation, said heater and said sensor portions each having terminals, said system further being positioned in direct communication with the fluid of interest, said resistive heater thereby being thermally coupled to said sensor via said fluid of interest;

adjustable electrical pulse producing means connected in energizing relation to said heater terminals for providing an energy input to the heater of a level and duration such that both intervals of transient and substantially steady-state elevated temperature conditions are induced in the sensor means via the fluid of interest;

first output means for providing an electrical potential output signal indicative of the temperature of said thermal sensor means;

means for determining the rate of change of temperature of said thermal sensor during a transient temperature interval based on a time interval between selected temperaturs indicated by said first output signal;

means for determining k of the fluid of interest based upon the sensor output at steady-state elevated sensor temperature; and means for determining $c_p$ of the fluid of interest based on k and the rate of change of the sensor output signal during a transient temperature interval.

3. The apparatus of claim 1 further comprising second output means for providing output signals indicative of k and $c_p$ of the fluid of interest.

4. The apparatus of claim 2 further comprising second output means for providing output signals indicative of k and $c_p$ of the fluid of interest.

5. The apparatus of claim 2 wherein said resistive heater and resistive sensor portions are the same.

6. The apparatus of claim 2 wherein said microbridge resistive heater and resistive sensor portions comprise a sensor-heater-gap-heater-sensor configuration.

7. The apparatus of claim 2 wherein said microbridge resistive heater and resistive sensor portions comprise a heater-gap-sensor configuration.

8. The apparatus of claim 2 wherein said resistive heater and resistive sensor means are provided with an outer insulating layer to reduce heat flow through solid media.

9. The apparatus of claim 2 wherein said first output means includes a Wheatstone bridge which includes said thermal sensor.

10. The apparatus of claim 2 wherein said means for determining the rate of change of temperature of said sensor means further comprises counting means for measuring said time interval required for said sensor temperature to rise or fall between two of more known temperature values represented by known values of said first output.

11. The apparatus of claim 10 including means for varying said temperature values.

12. A method for determining thermal conductivity, k, and specific heat, $c_p$, of a fluid of interest comprising the steps of:

providing proximately positioned heater and thermal sensor means coupled by said gaseous fluid of interest, said sensor means being one having a temperature sensitive output;

providing an energy input pulse to the heater means of a level such that an interval of transient temperature change is correspondingly produced in the sensor means;

providing an energy input to the heater means of a duration such than an interval of substantially steady-state elevated temperature is correspondingly produced in the sensor means;

obtaining a sensor output related to the elevated temperature of the sensor at said steady-state temperature;

determining k of the fluid of interest based upon the sensor output at said steady-state elevated sensor temperature;

determining the rate of change of sensor output during a portion of said transient temperature change in the sensor; and determining $c_p$ of the fluid of interest based upon the rate of change of sensor output during said interval of transient temperature change and k.

13. The method of claim 12 wherein the heater and sensor means are electrical resistance elements and the input to the heater is in the form of an electric pulse of elevated voltage level and known duration.

14. The method of claim 12 where the fluid is gas.

15. A method for determining thermal conductivity, k, and specific heat, $c_p$, of a fluid of interest comprising the steps of:

providing proximately positioned microbridge thin film electrical resistance heater and thermal sensor means coupled by said fluid of interest, said sensor means being one having a temperature sensitive electrical output signal;

providing an electrical energy input pulse to the heater means of a level such that the sensing means experiences an interval of transient temperature change and of a duration such that the sensing means experiences an interval of substantially steady-state elevated temperature;

obtaining a sensor output related to the sensor temperature at said steady-state elevated temperature;

determining k of the fluid of interest based upon the electrical sensor output signal at said steady-state elevated sensor temperature;

obtaining an output related to the rate of change of temperature of the sensor during said transient temperature change; and determining $c_p$ of the gas of interest based on the rate of change of sensor output during said transient temperature change in said sensor and k.

16. The method of claim 15 wherein $c_p$ is determined with respect to an upward transient temperature change in the sensor.

17. The method of claim 15 wherein $c_p$ is determined with respect to a downward transient temperature change in the sensor.

18. The method of claim 15 where the fluid is a gas.

19. The method of claim 15 wherein said output related to the rate of change of temperature of the sensor is obtained by the step of measuring the time interval for the sensor temperature to change between two known temperatures.

20. The method of claim comprising the step of adjusting the two known temperatures used for determining the rate of change of temperature said thermal sensor to produce the most accurate results for a given fluid of interest.

21. A method for determining thermal conductivity, k, of a fluid of interest comprising the steps of:

providing proximately positioned microbridge electrical resistance heater and thermal sensor means coupled by said fluid of interest, said thermal sensor having a temperature sensitive output signal;

providing and electrical energy input pulse to the heater means of a known level and of a known duration such that the thermal sensor means achieves an interval of substantially steady-state elevated temperature;

obtaining a sensor output signal related to the sensor temperature of at said elevated steady-state temperature; and determining k of the fluid of interest based upon the sensor output at said steady-state elevated sensor temperature substantially approximated by $$k = a_4 U + a_5$$

where U is the sensor output and $a_4$ and $a_5$ are constants.

22. The method of claim 21 wherein the constants $a_4$ and $a_5$ are determined based on a known value of k for one or more fluids.

23. The method of claim 21 where the fluid is a gas.

24. A method of determining thermal conductivity, k, and specific heat, $c_p$, of a fluid of interest comprising the steps of:

providing proximately positioned microbridge electrical resistance heater and thermal sensor means coupled by said fluid of interest, said thermal sensor having a temperature sensitive output signal;

providing an electrical energy input pulse to the heater means of a known level and of a known duration such that the thermal sensor means achieves an interval of substantially steady-state elevated temperature;

obtaining a sensor output signal related to the sensor temperature of at said elevated steady-state temperature;

determining k of the fluid of interest based upon the thermal sensor output at said steady-state elevated sensor temperature substantially approximated by $$k = a_4 U + a_5$$

where U is the sensor output and $a_4$ and $a_5$ are constants;

obtaining an output indicative of the rate of change of temperature of the thermal sensor means by measuring the time interval for the thermal sensor temperature to change between two known temperatures; and determining $c_p$ of the fluid of interest based on the relation $$c_p P/P_o = a_1(t_2 - t_1)k + a_2(t_2 - t_1) - a_3$$

where $a_1$, $a_2$ and $a_3$ are constants

P = pressure (psia)

$P_o$ = reference pressure (psia)

$(t_2 - t_1)$ = measured time span for the temperature of the thermal sensor to sensor to change between known temperatures.

25. The method of claim 24 wherein $c_p$ is determined with respect to an upward transient temperature change in the sensor.

26. The method of claim 24 wherein $c_p$ is determined with respect to a downward transient temperature change in the sensor.

27. The method of claim 24 comprising the step of adjusting the two known temperatures used for determining the rate of change of temperature said thermal sensor to produce the most accurate results for a given fluid of interest.

28. The method of claim 24 where the fluid is a gas.

* * * * *